(12) United States Patent
Campos Del Olmo et al.

(10) Patent No.: US 8,133,001 B2
(45) Date of Patent: Mar. 13, 2012

(54) DEVICE FOR OVERTURNING CONTAINERS

(75) Inventors: Antonio Campos Del Olmo, Madrid (ES); Mario Ugolini, Madrid (ES)

(73) Assignee: Ares Trading S.A., Aubonne (CH)

( * ) Notice: Subject to any disclaimer, the term of this patent is extended or adjusted under 35 U.S.C. 154(b) by 396 days.

(21) Appl. No.: 12/306,739

(22) PCT Filed: Aug. 21, 2007

(86) PCT No.: PCT/EP2007/058664
§ 371 (c)(1),
(2), (4) Date: Feb. 5, 2009

(87) PCT Pub. No.: WO2008/023010
PCT Pub. Date: Feb. 28, 2008

(65) Prior Publication Data
US 2009/0196726 A1 Aug. 6, 2009

(30) Foreign Application Priority Data
Aug. 23, 2006 (ES) .................................. 200602238

(51) Int. Cl.
*B21C 47/24* (2006.01)
*B01F 7/00* (2006.01)

(52) U.S. Cl. ........ 414/776; 414/754; 414/783; 414/771; 366/213

(58) Field of Classification Search ............... 198/403, 198/404; 222/164, 166; 366/213; 414/419–421, 414/754, 758, 764, 774, 776, 783; 435/395
See application file for complete search history.

(56) References Cited

U.S. PATENT DOCUMENTS

| | | | | | |
|---|---|---|---|---|---|
| 2,260,697 | A | * | 10/1941 | Allen | 414/421 |
| 2,979,217 | A | * | 4/1961 | Tomasovich | 414/641 |
| 3,062,388 | A | * | 11/1962 | Hunter | 414/744.7 |
| 3,127,210 | A | * | 3/1964 | Schreiber | 294/116 |
| 3,777,453 | A | * | 12/1973 | Zimmermann et al. | 53/251 |
| 3,893,887 | A | | 7/1975 | Smith et al. | |
| 4,087,012 | A | * | 5/1978 | Fogg | 414/419 |
| 5,152,655 | A | * | 10/1992 | Pipes | 414/344 |
| 5,281,076 | A | * | 1/1994 | Lehman | 414/607 |
| 5,424,622 | A | * | 6/1995 | Keller et al. | 318/375 |
| 6,062,724 | A | * | 5/2000 | Habicht | 366/209 |
| 6,976,823 | B2 | * | 12/2005 | Maeda | 414/759 |
| 2004/0025909 | A1 | | 2/2004 | Lopes | |
| 2008/0068924 | A1 | * | 3/2008 | Midas et al. | 366/213 |

FOREIGN PATENT DOCUMENTS

| | | |
|---|---|---|
| EP | 1028075 A1 | 8/2000 |
| EP | 1225139 A1 | 7/2002 |
| FR | 2815621 | 4/2002 |
| JP | 04152089 A * | 5/1992 |

* cited by examiner

*Primary Examiner* — Gregory Adams
(74) *Attorney, Agent, or Firm* — Saliwanchik, Lloyd & Eisenschenk (57) ABSTRACT

The invention relates to a device (1) for overturning containers (2), particularly roller bottles intended for cell cultures, characterized in that it comprises a rotation actuator (3) associated by means of a transmission shaft (13) to a reducer (4) and a dynamic brake (5), a support (17) and rods (7) gripping the container (2), said support (17) being joined to the rotation actuator (3) by means of a shifter (16) of the transmission shaft (13) of the mentioned rotation actuator (3), the rotation actuator (3) being actuated by means of a pneumatic foot pedal (18), and the mentioned rotation actuator (3) in turn being associated to a timer (19) indicating the end of the overturning time of the container (2).

12 Claims, 11 Drawing Sheets

SECTION A A'

DEVICE FOR OVERTURNING CONTAINERS

CROSS-REFERENCE TO RELATED APPLICATION

This application is the U.S. national stage application of International Patent Application No. PCT/EP2007/058664, filed Aug. 21, 2007, the disclosure of which is hereby incorporated by reference in its entirety, including all figures, tables and amino acid or nucleic acid sequences.

FIELD OF THE INVENTION

The present invention relates to an improved device for overturning containers, particularly containers intended for cell cultures.

BACKGROUND OF THE INVENTION

The techniques for the large-scale higher organism cell culturing used today are divided into two large groups: those in which the cells are suspended in a stirred nutrient medium or those in which the cells adhere to a solid support bathed with the nutrient medium. Cells which adhere to a solid support are generally referred to as "anchorage dependent" cells. The nutrient medium is generally a liquid comprising a basal nutrient mixture and can also contain a biological extract e.g. serum derived from mammalian blood, in the absence of which the cells would no longer be viable and they would lose their ability to proliferate. In the past years, cell culture media have been developed, in which cells can be grown and maintained in the absence of serum. These media are generally called serum-free media.

For anchorage dependent cells one of the most frequently used methods today consists of using so-called roller bottles as the culture container, which bottles are usually arranged on roller racks which provide the bottles the corresponding rotation. In these roller bottles, the cells adhere to the inner wall of the bottle such that the continuous rotation thereof keeps the cell layer (the thickness of the cell layer is often equivalent to one of them, and in this case it is referred to as "single-layer") in contact with the nutrient medium. When the cells are cultured in said media, they remain viable for a finite period until one or more nutrients of the medium is used up. Once this time has passed it is necessary to empty and refresh or replace the content of the nutrient medium inside the roller bottles, without entraining or damaging the aforementioned single-layer, which means that emptying movements must be extremely gentle and careful.

Based on the description provided above, emptying these bottles today, an operation, which in addition must be carried out very frequently with large-scale cultures, is carried out by hand or by means of very expensive and complex robots. Overturning the bottles by hand causes problems with tendonitis, discomfort in the hands and shoulders and the so-called carpal tunnel syndrome in the operators responsible for carrying out this operation with a high daily frequency. When the bottles are overturned using robots there is a problem due to the lack of gentleness in said movement, as well as the existence of vibrations, which results in the single-layer becoming detached or damaged on many occasions.

The present invention aims to solve the limits set forth above.

SUMMARY OF THE INVENTION

The present invention aims to solve the aforementioned problems by developing a device for overturning containers, particularly roller bottles intended for cell cultures, such that the cell culture inside the roller bottles is refreshed without entraining or damaging the cell culture layer or single-layer since the overturning is carried out with extremely gentle and careful movements. Furthermore, by means of the device of the invention the operator simply places the roller bottle with the culture medium that must be replaced in the device and the device carries out the complete overturning operation without the operator having to be involved again. Therefore, the invention provides a simple, inexpensive and effective device, which prevents discomforts for operators.

These and other features and advantages of the present invention will be inferred from the following detailed description of the illustrative and non-limiting embodiments thereof in relation to the attached figures.

DETAILED DESCRIPTION OF THE PREFERRED EMBODIMENTS

Figure 1:
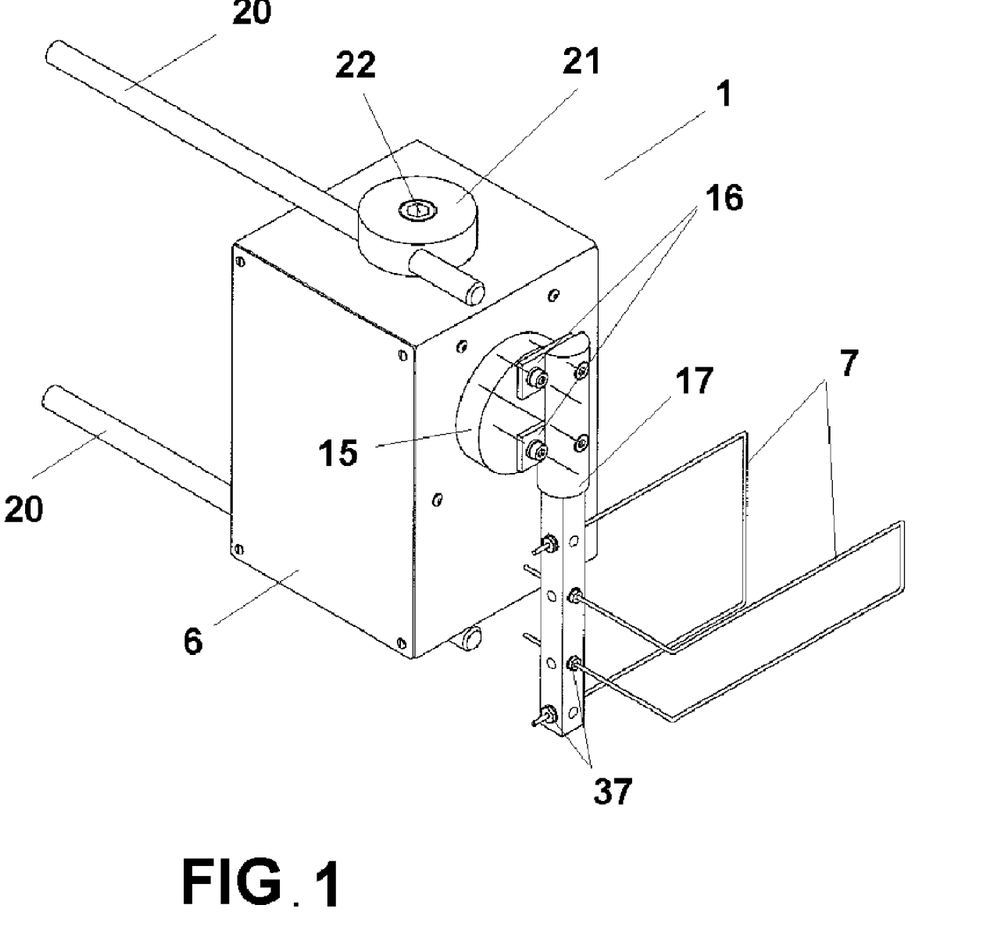
FIGS. 1 and 2 are schematic views of the device for overturning containers according to the invention.
Figure 2:
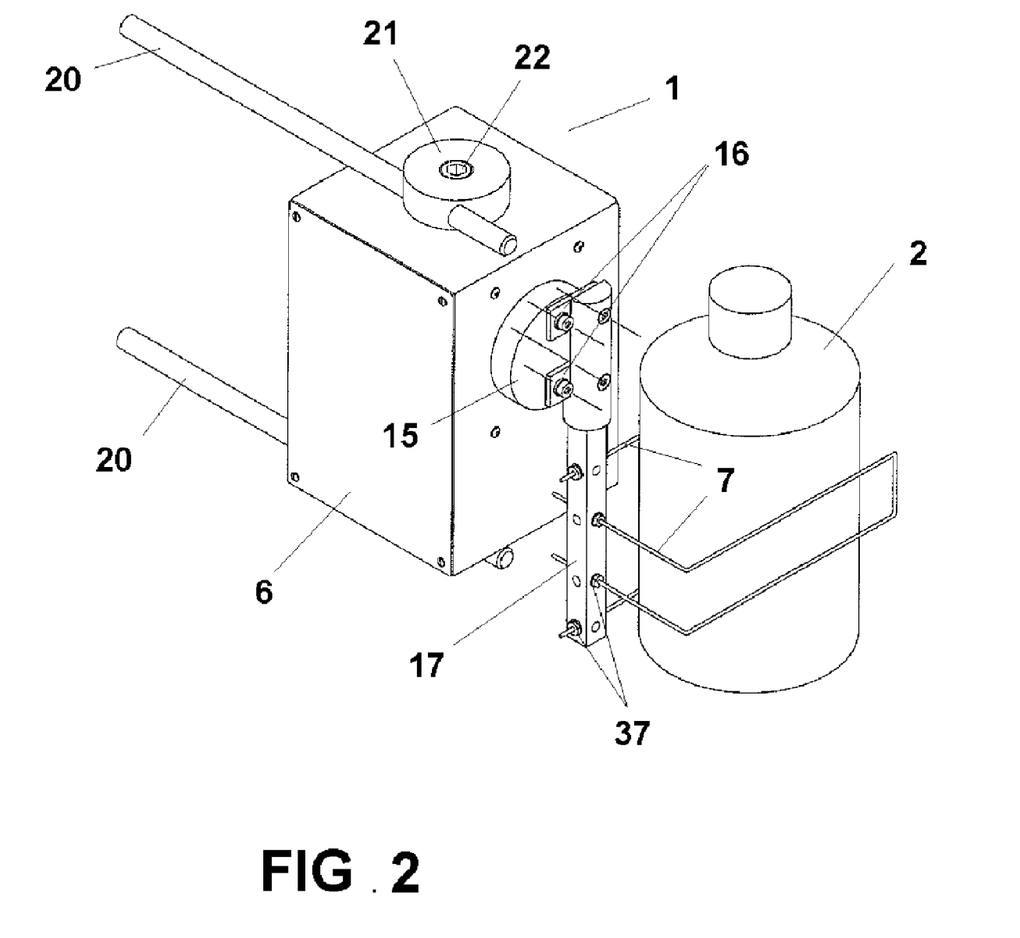
Figure 3:
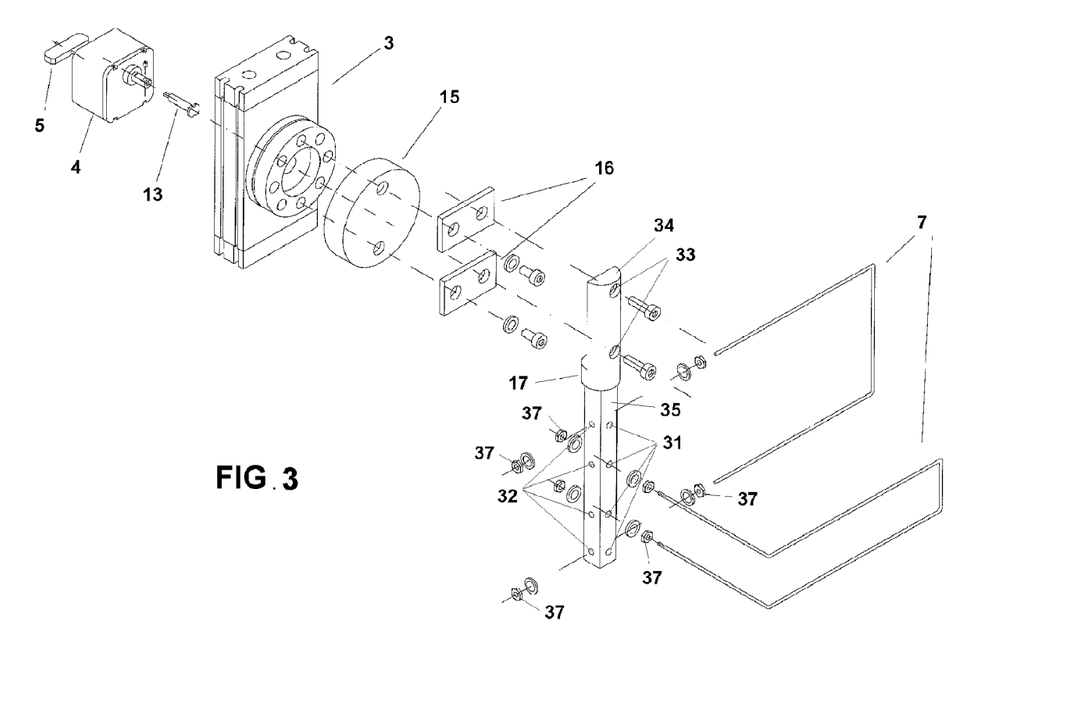
FIG. 3 is an exploded view of the main actuating elements of the device for overturning containers according to the invention.

As shown in FIGS. 1 to 3, the device 1 for overturning containers 2 according to the invention comprises a casing 6 enclosing a preferably pneumatic, rack-pinion type rotation actuator 3 associated by means of a transmission shaft 13 to a reducer 4 and a dynamic brake 5; a support 17 and rods 7 associated to said support 17 gripping the container 2, said support 17 being joined to the rotation actuator 3 by means of a shifter 16 of the transmission shaft arranged on a cover 15 of the mentioned rotation actuator 3.

Figure 12:
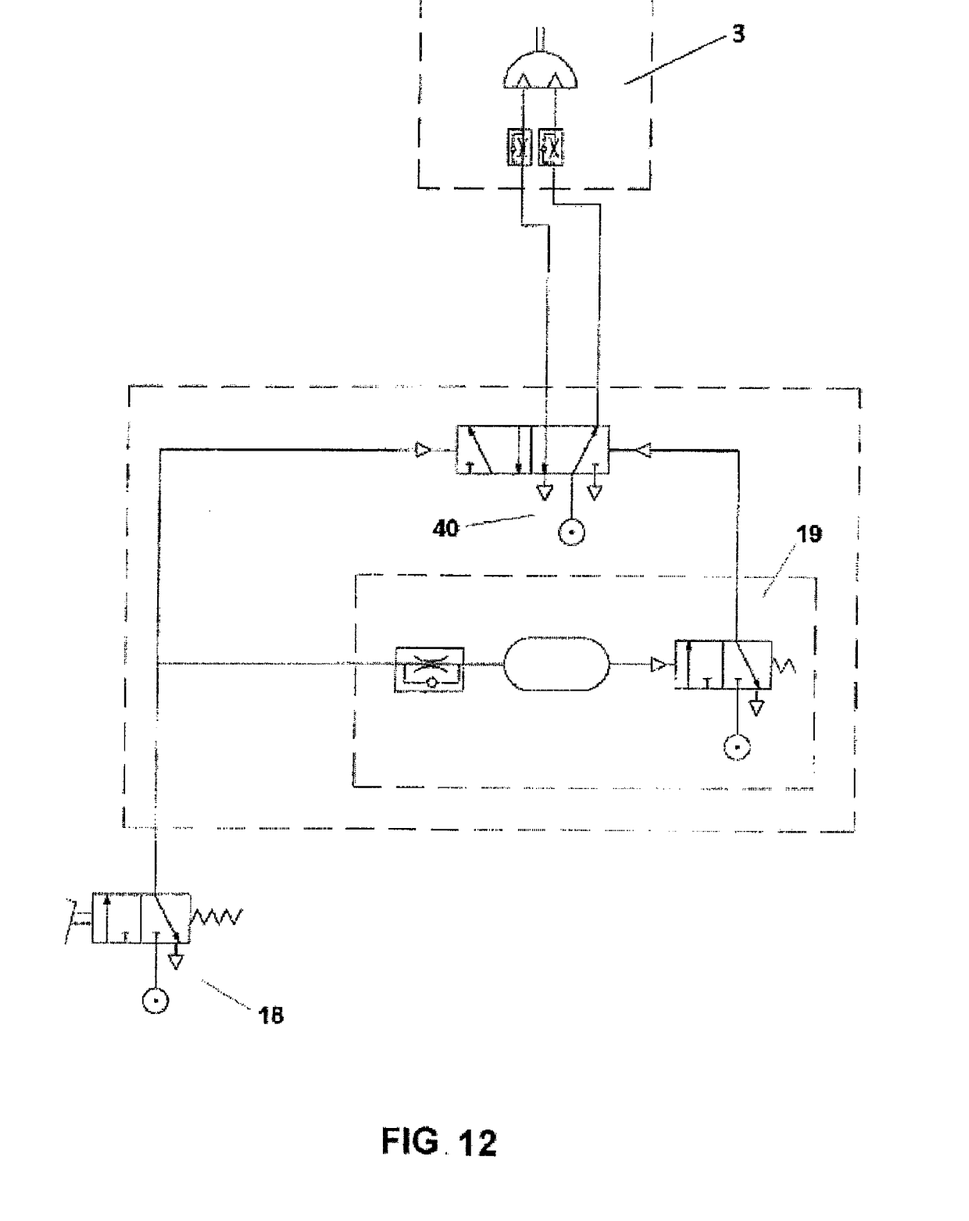
FIG. 12 is a diagram of the pneumatic circuit associated to the device for overturning containers according to the invention.

Possible vibrations of the rotation actuator 3 according to the invention are prevented by means of using the reducer 4 and the pneumatic brake 5 such that the movement that the mentioned actuator 3 causes for the containers 2 when they are overturned is gently and very precise, thus preventing possible unwanted detachments of the culture cells contained in the mentioned containers 2. As shown in FIG. 12, the preferably pneumatic rotation actuator 3 is operated by means of a foot pedal 18 associated to a timer 19 indicating the end of the overturning time (previously calculated and timed) of the container 2, therefore the device 1, together with the support 17 and the rods 17, return to their initial position. In accordance with the invention, the foot pedal 18 can be pneumatic or electronic. The timer 19 can also be pneumatic or, preferably, electronic.

Figure 4A:
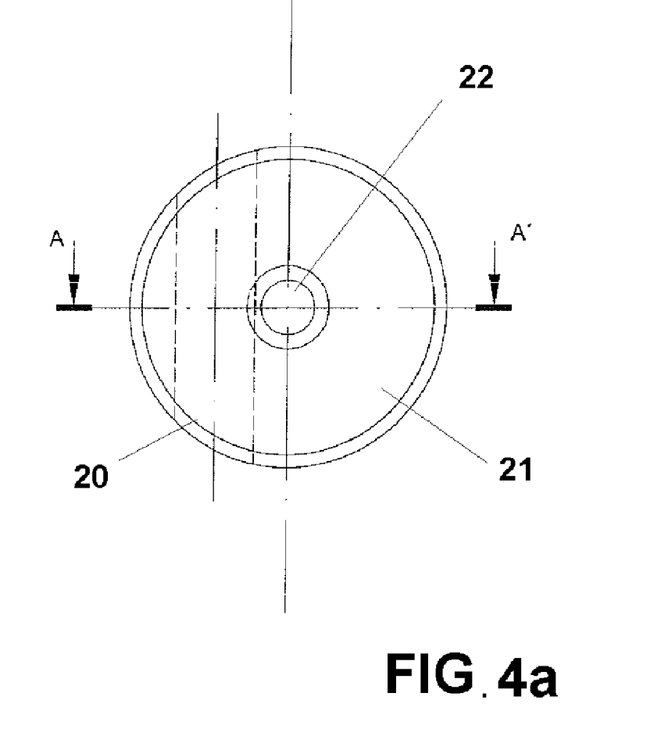
FIGS. 4a and 4b are plan and sectional views of the clamping of the casing of the device for overturning containers according to the invention.
Figure 4B:
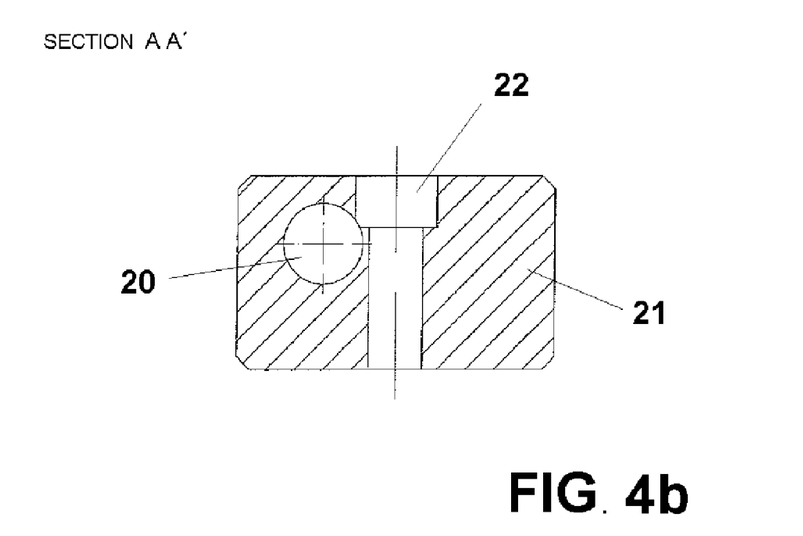

As can be inferred from FIGS. 4a and 4b, the casing 6 of the device 1 for overturning containers 2 is clamped to gripping rods 20 through preferably circular clamping parts 21 and made of stainless steel, comprising an eccentric borehole for the passage of the clamping rods 20, and a central borehole 22 for fixing the mentioned parts 21, together with the gripping rods 20, to the casing 6 of the device 1.

Figures 5A, 5B:
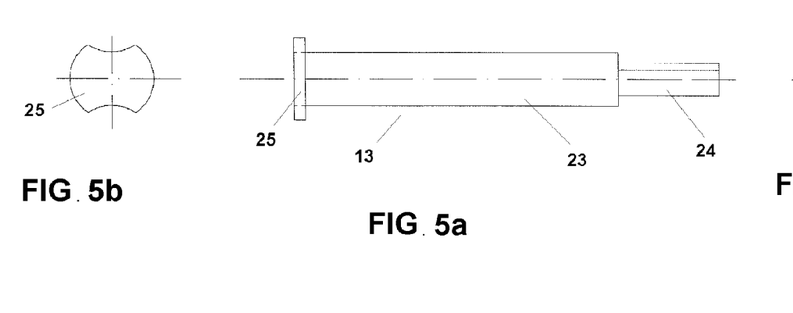
FIGS. 5a, 5b and 5c are views of the transmission shaft of the device for overturning containers according to the invention.
Figure 5C:
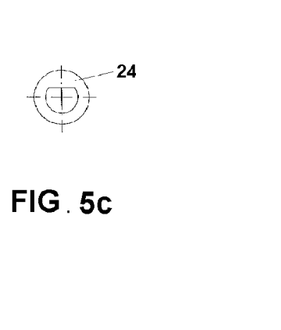
Figure 6:
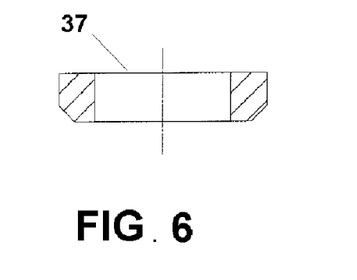
FIG. 6 is a sectional view of the clamping washers for clamping the bars of the device for overturning containers according to the invention.
Figure 7A:
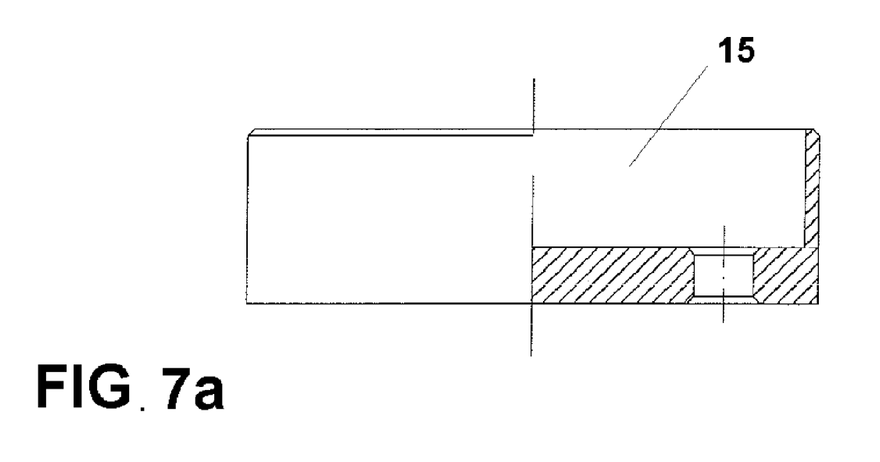
FIGS. 7a and 7b are plan and sectional views of the cover of the rotation actuator of the device for overturning containers according to the invention.
Figure 7B:
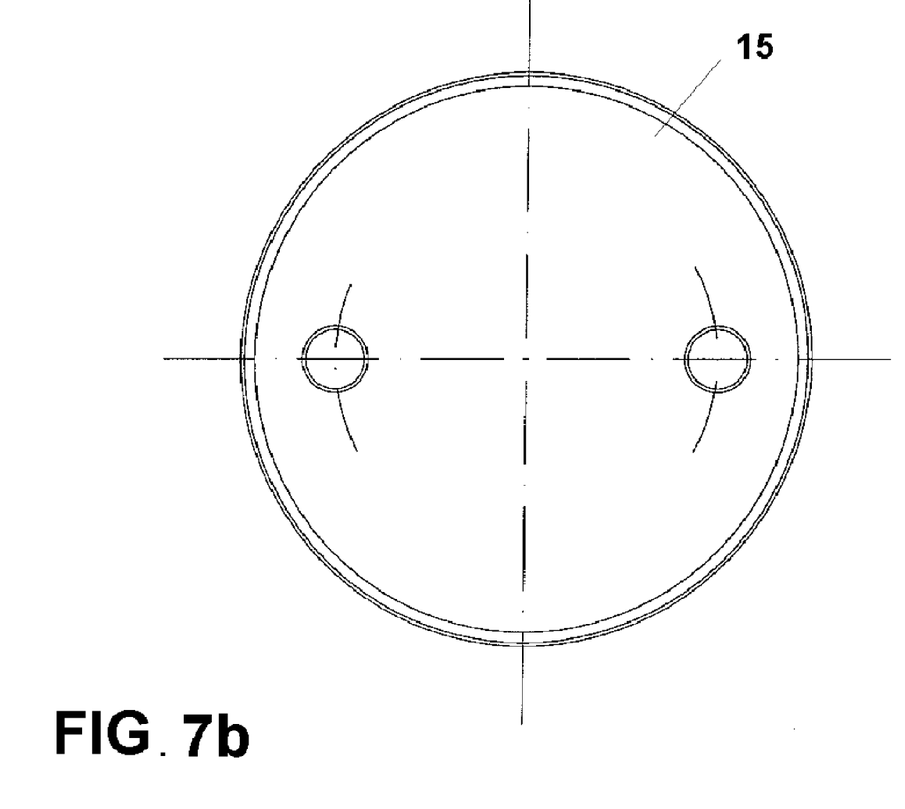
Figure 8:
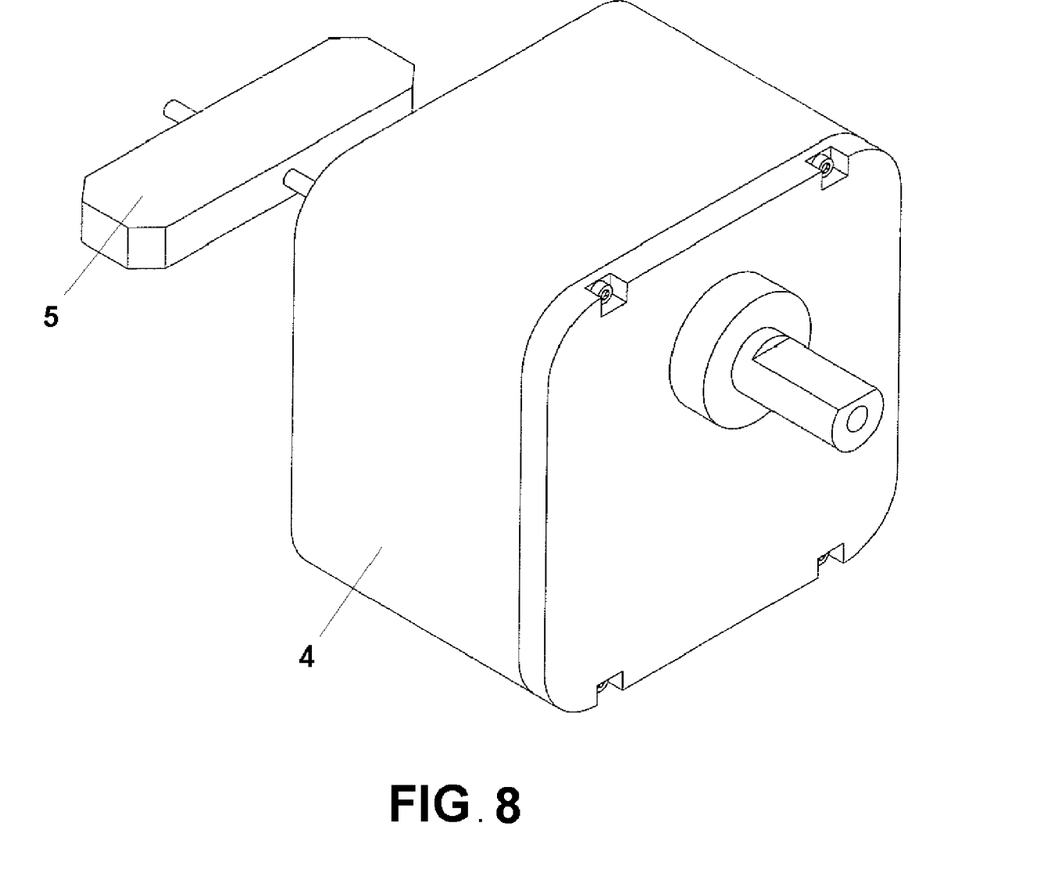
FIG. 8 is a schematic view of the dynamic brake and the reducer of the device for overturning containers according to the invention.

The dynamic brake 5 and the reducer 4 are joined to the rotation actuator 3 by means of a transmission shaft 13, preferably made of stainless steel, comprising, as can be inferred from FIGS. 5a, 5b and 5c, a central part or shaft 23 with a circular section, a shall 24 with an also circular section engaging the reducer 4, which has a smaller diameter than that of the mentioned shaft 23 and is concentric in relation to the latter, and a disc 25 with a multi-shape section engaging the rotation actuator 3.

Figure 9:
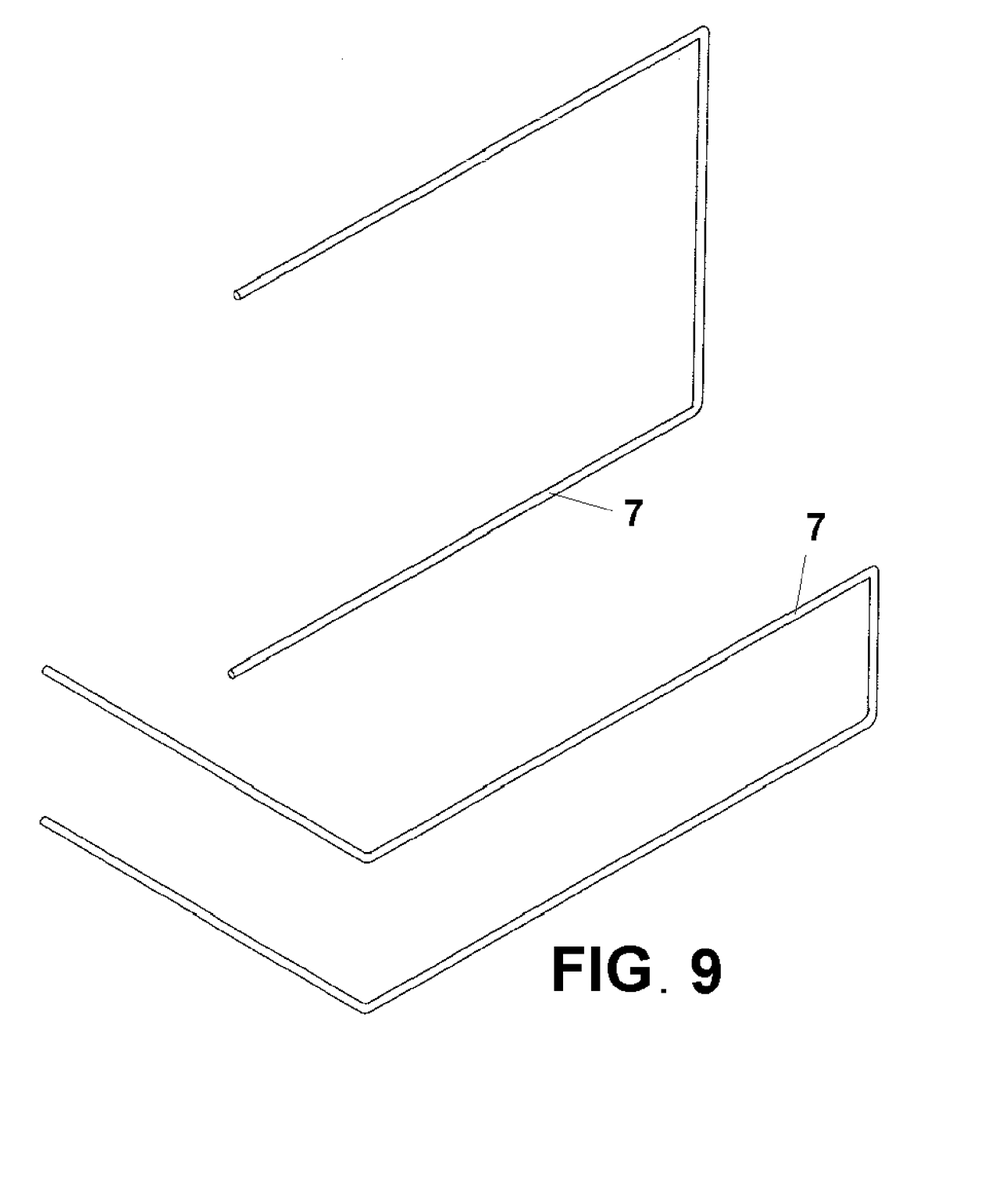
FIG. 9 is a schematic view of the rods of the device for overturning containers according to the invention.
Figure 10A:
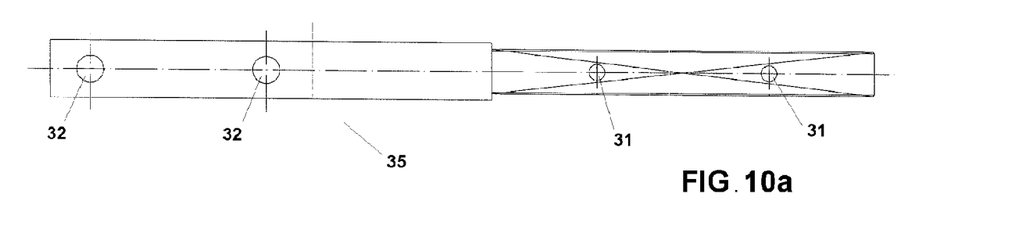
FIGS. 10a and 10b are plan views of the support for the rods of the device for overturning containers according to the invention.
Figure 10B:
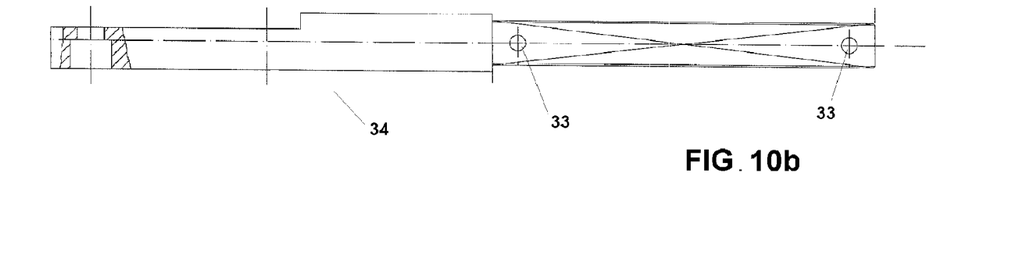

As shown in FIGS. 9, 10a and 10b, the gripping rods 7 of the container 2 which is to be overturned, preferably made of stainless steel, are fixed on a support 17, preferably made of stainless steel also, comprising a lower part 35 with several front boreholes 31 in which it grips the first of the rods 7, and several side boreholes 32 in which it grips the second one of the rods 7, and an upper part 34 comprising boreholes 33 through which the mentioned support 17 is joined to the rotation actuator 3, through the shifter 16 of the transmission shaft and of the cover 15.

As can be seen in FIG. 3 and in the detail view of FIG. 5, the gripping rods 7 for gripping or supporting the container 2 are fixed to the support 17 using washers 37 preferably made of bronze.

Figure 11A:
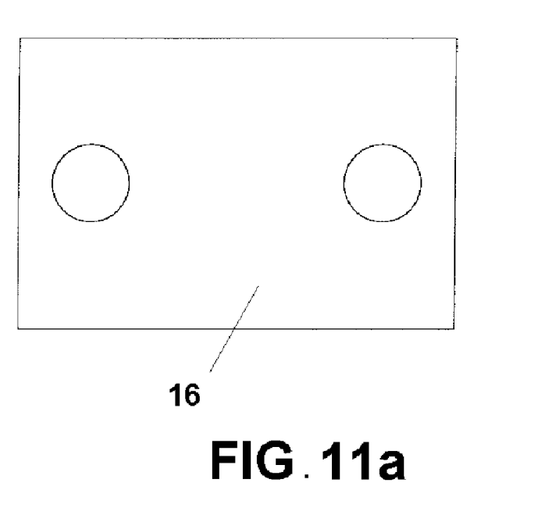
FIGS. 11a and 11b are plan and sectional views of the shifter of the transmission shaft of the device for overturning containers according to the invention.
Figure 11B:
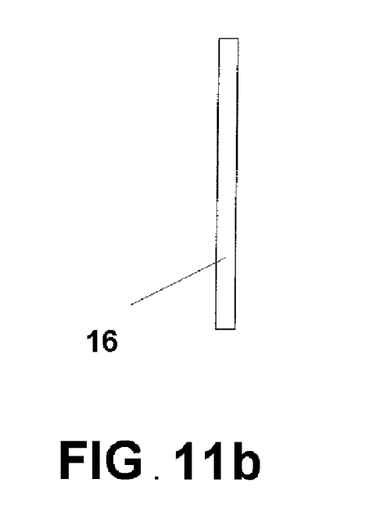

FIGS. 11a and 11b show the shifter 16 of the transmission shaft comprising a pair of flat plates, preferably made of stainless steel, each of them comprising a pair of boreholes, one of which fixes said flat plate to the cover 15 of the actuator while the other borehole fixes the mentioned shifter 16 of the transmission shaft to the rod support 17. The shifter is intended to move the center of rotation of the rod support 17 with respect to the center of rotation of the cover 15 so as to adapt the overturning device 1 object of the invention to the work station. The cover 15 of the rotation actuator 3 comprises a pair of boreholes for its fixing to the mentioned actuator 3, preferably being made of stainless steel.

As can be seen in FIG. 12, the pneumatic circuit associated to the rotation actuator 3 of the overturning device 1 of the invention makes said rotation actuator 3 to work similarly to that of a double acting pneumatic cylinder. The mentioned rotation actuator 3 is actuated by a 5/2-way valve 40 controlled by a preferably pneumatic 3/2-way foot pedal 18 that is usually closed for forward movement, and by a preferably pneumatic timer 19 for backward movement.

Therefore the design of the support 17 and its support rods 7 for supporting the containers 2 is simple and easy to use for operators. The overturning device 1 according to the invention is likewise preferably located in an aseptic area so during operation thereof, no detachment of particles whatsoever that may contaminate said aseptic area has to occur. Therefore the outer parts of the mentioned device 1 according to the invention are preferably made of stainless steel, thus aiding in the cleaning of said outer parts with agents that do not cause corrosive effects on the aforementioned.

The invention further relates to a process for operating the overturning device 1 comprising the steps of:
1. Placing the container 2 in the support rods 7 of the overturning device 1;
2. actuating the rotation actuator 3 of the overturning device 1 by means of a foot pedal 18;
3. beginning the container 2 overturning process;
4. timing the end of the container 2 overturning process;
5. returning the container 2, together with the device 1, to its initial position;
6. removing the container 2 from the support rods 7.

The invention further relates to the use of the overturning device (1) of the invention for changing a cell culture medium in a roller bottle comprising a cell culture of anchorage dependent cells.

Examples of anchorage dependent cells that can be cultured in roller bottles include mammalian cells such as 3T3 cells, COS cells, human osteosarcoma cells, MRC-5 cells, BHK cells, VERO cells, CHO cells, rCHO-tPA cells, rCHO-Hep B Surface Antigen cells, NS0 cells, HEK 293 cells, rHEK 293 cells, C127 cells, normal human fibroblast cells, stroma cells, hepatocytes or PER.C6 cells.

In a preferred embodiment, the cell culture medium is a serum-free cell culture medium.

Examples for commercially available serum-free cell culture media known in the art include, e.g., SFM 90 (JRH, 67350), SFM 90.1 (JRH, 67350), Supmed300 or Supmed300 modified (JRH, 67350), DMEM (Gibco, 7490571), DMEM/F12 (Gibco, 99.5043), SFM CHO 3a (BioWhittaker), CHO PFM (Sigma, C6970), ProCHO 5, EX-CELL media such as EX-CELL 302 (JRH, Catalogue No. 14312-1000M) or EX-CELL 325 (JRH, Catalogue No. 14335-1000M), CHO-CD3 (Sigma, Catalogue No. C-1490), CHO III PFM (Gibco, Catalogue No. 96-0334SA), CHO-S-SFM II (Gibco, Catalogue No. 12052-098), CHO-DHFR (Sigma, Catalogue No. C-8862), ProCHO 5 (Cambrex, Catalogue No. BE12-766Q), SFM4CHO (HyClone, Catalogue No. SH30549.01), Ultra CHO (Cambrex, Catalogue No. 12-724Q), HyQ PF CHO (HyClone, Catalogue No. SH30220.01), HyQ SFX CHO (HyClone, Catalogue No. SH30187.01), HyQ CDM4CHO (HyClone, Catalogue No. SH30558.01), IS CHO-CD (Irvine Scientific, Catalogue No. #91119), IS CHO-V (Irvine Scientific, Catalogue No. #9197) and derivatives thereof.

In a further preferred embodiment, the anchorage dependent cells express a recombinant protein.

Such recombinant proteins include e.g. chorionic gonadotropin, follicle-stimulating hormone, lutropin-choriogonadotropic hormone, thyroid stimulating hormone, growth hormone, in particular human growth hormone, interferons (IFN), such as IFN-α, IFN-β or IFN-γ, interferon receptors (e.g., interferon gamma receptor), TNF receptors p55 and p75, TACI-Fc fusion proteins, interleukins (e.g., interleukin-2, interleukin-11), interleukin binding proteins (e.g., interleukin-18 binding protein), erythropoietin, granulocyte colony stimulating factor, granulocyte-macrophage colony-stimulating factor, pituitary peptide hormones, menopausal gonadotropin, insulin-like growth factors (e.g., somatomedin-C), keratinocyte growth factor, glial cell line-derived neurotrophic factor, thrombomodulin, basic fibroblast growth factor, insulin, Factor VIII, somatropin, bone morphogenetic protein-2, platelet-derived growth factor, hirudin, epoietin, recombinant LFA-3/IgG1 fusion protein, glucocerebrosidase, and muteins, fragments, soluble forms, functional derivatives, fusion proteins thereof. Furthermore, recombinant proteins that can be expressed by anchorage dependent cells can be antibodies, such as Abciximab, Rituximab, Basiliximab, Daclizumab, Palivizumab, Infliximab, Trastuzumab, Alemtuzumab, Adalimumab, Cetuximab, Efalizumab, Ibritumomab, Bevacizumab, or Omalizumab.

Even though the present invention has been described completely in relation to preferred embodiments, these embodiments are not considered to be limiting and any modifications comprised within the scope defined by the following claims can be introduced.

The invention claimed is:

1. A device (1) for overturning containers (2), the device (1) comprising:
   a rotation actuator (3) including a transmission shaft (13);
   a reducer (4) connected to a dynamic brake (5) and joined to the rotation actuator (3) via one end of the transmission shaft (13);
   a support (17) joined to the rotation actuator (3) by a shifter (16) of the transmission shaft (13) of the rotation actuator (3), and
   rods (7) fixed to the support (17) for gripping the container (2),
   wherein the shifter (16) of the transmission shaft (13) of the rotation actuator (3) comprises a pair of flat plates fixing the shifter (16) at one side to the rotation actuator (3) and at the other end to the support (17).

2. The device (1) for overturning containers (2) according to claim 1, wherein the rotation actuator (3) is pneumatic.

3. The device (1) for overturning containers (2) according to claim 1, wherein the rotation actuator (3) is a rack and pinion type actuator.

4. The device (1) for overturning containers (2) according to claim 1, further comprising:
   a foot pedal (18) for operating the rotation actuator (3); and
   a timer (19) indicating an end of an overturning time for the container (2).

5. The device (1) according to claim 4, wherein the foot pedal is pneumatic.

6. The device (1) according to claim 4, wherein the foot pedal is electronic.

7. The device (1) according to claim 4, wherein the timer is pneumatic.

8. The device (1) according to claim 4, wherein the timer is electronic.

9. A process for operating a device (1) according to claim 1 comprising the steps of:
   a) placing the container (2) in the support rods (7) of the overturning device (1);
   b) actuating the rotation actuator (3) of the overturning device (1) using a foot pedal (18);
   c) beginning the container (2) overturning process;
   d) timing the end of the container (2) overturning process;
   e) returning the container (2), together with the device (1), to its initial position; and
   f) removing the container (2) from the support rods (7).

10. A method of removing cell culture medium from a container comprising decanting a container comprising cell culture medium and culture of anchorage dependent cells using a device according to claim 1.

11. The method according to claim 10, wherein the cell culture medium is a serum-free cell culture medium.

12. The method according to claim 10, wherein the anchorage dependent cells express a recombinant protein.

* * * * *

UNITED STATES PATENT AND TRADEMARK OFFICE
CERTIFICATE OF CORRECTION

| | | |
|---|---|---|
| PATENT NO. | : 8,133,001 B2 | Page 1 of 1 |
| APPLICATION NO. | : 12/306739 | |
| DATED | : March 13, 2012 | |
| INVENTOR(S) | : Antonio Campos Del Olmo and Mario Ugolini | |

It is certified that error appears in the above-identified patent and that said Letters Patent is hereby corrected as shown below:

Column 3,
Line 7, "and the rods 17" should read --and the rods 7--.
Line 22, "a shall 24" should read --a shaft 24--.

Column 6,
Lines 14-15, "A process for operating a device (1) according to claim 1, comprising the
steps of:"
should read
--A process for operating a device (1) comprising providing a device
according to claim 1, and wherein the process further comprises steps of:--.

Signed and Sealed this
Fifth Day of June, 2012

David J. Kappos
*Director of the United States Patent and Trademark Office*